United States Patent
Seo et al.

(10) Patent No.: US 11,253,498 B2
(45) Date of Patent: Feb. 22, 2022

(54) PHARMACEUTICAL COMPOSITION FOR TREATMENT OF BONE-RELATED DISEASE

(71) Applicant: Nexyon Biotech Co., Ltd., Seoul (KR)

(72) Inventors: Jung Taek Seo, Seoul (KR); Seok Jun Moon, Seoul (KR); Sung Jin Kim, Seoul (KR)

(73) Assignee: Nexyon Biotech Co., Ltd., Seoul (KR)

( * ) Notice: Subject to any disclaimer, the term of this patent is extended or adjusted under 35 U.S.C. 154(b) by 119 days.

(21) Appl. No.: 16/617,757

(22) PCT Filed: May 30, 2018

(86) PCT No.: PCT/KR2018/006174
§ 371 (c)(1),
(2) Date: Nov. 27, 2019

(87) PCT Pub. No.: WO2018/221966
PCT Pub. Date: Dec. 6, 2018

(65) Prior Publication Data
US 2020/0188353 A1    Jun. 18, 2020

(30) Foreign Application Priority Data

Jun. 1, 2017   (KR) .......................... 10-2017-0068400
Jan. 16, 2018  (KR) .......................... 10-2018-0005406
May 16, 2018   (KR) .......................... 10-2018-0055737

(51) Int. Cl.
    *A61K 31/37*   (2006.01)
    *A61P 19/10*   (2006.01)
    *A61K 45/06*   (2006.01)

(52) U.S. Cl.
    CPC .............. *A61K 31/37* (2013.01); *A61K 45/06* (2013.01); *A61P 19/10* (2018.01)

(58) Field of Classification Search
    CPC ................................ A61K 31/37; A61P 19/10
    See application file for complete search history.

(56) References Cited

U.S. PATENT DOCUMENTS 5,340,586 A   8/1994  Pike et al.
6,013,642 A   1/2000  Foulkes et al.

FOREIGN PATENT DOCUMENTS

KR   20140018814 A   2/2014
WO      01/52857 A1  7/2001
WO   2014021694 A1   2/2014

OTHER PUBLICATIONS

International Search Report, International Patent Application No. PCT/KR2018/006174, dated Sep. 28, 2018.
International Preliminary Examination Report, International Patent Application No. PCT/KR2018/006174, dated Dec. 3, 2019.
S.L. Nand et al., "Bleeding Pattern and Endometrial Changes During Continuous Combined Hormone Replacement Therapy," Obstetrics & Gynecology, 91(5), 678-684 (1998).
G.R. Mundy, "Regulatory mechanisms of osteoclast differentiation and function," J. Bone Miner. Metab., 14, 59-64 (1996).
C. Deal, "Potential new drug targets for osteoporosis," Nat. Clin. Pract. Rheumatol., 5(1), 20-7 (2009).
K. Vaananen, "Mechanism of osteoclast mediated bone resorption—rationale for the design of new therapeutics," Adv. Drug Deliv. Rev., 57(7), 959-71 (2005).
C.A. Strott et al., "Cholesterol sulfate in human physiology: what's it all about?," J. Lipid Res., 44(7), 1268-78 (2003).
L.T. Shuster et al., "Premature menopause or early menopause: long-term health consequences," Maturitas, 65(2), 161-66 (2010).
M.B. Dobbs et al., "Osteoporosis: the increasing role of the orthopaedist," Iowa Orthop. J., 19, 43-52 (1999).
A. Purohit et al., "Steroid sulfatase inhibitors for estrogen- and androgen-dependent cancers," J. Endocrinol., 212(2), 99-110 (2012).
P.A. Foster et al., "In vivo efficacy of STX213, a second-generation steroid sulfatase inhibitor, for hormone dependent breast cancer therapy," Clin. Cancer Res., 12(18), 5543-49 (2006).
O. Hanyu et al., "Cholesterol sulfate induces expression of the skin barrier protein filaggrin in normal human epidermal keratinocytes through induction of RORα," Biochem. Biophys. Res. Commun., 428(1), 99-104 (2012).
Lagrelius A. "Treatment with Oral Estrone Sulphate in the Female Climacteric." Acta. Obstet Gyneocol. Scand. 1981, 60, p. 481-488.

*Primary Examiner* — Kevin E Weddington
(74) *Attorney, Agent, or Firm* — McDonnell Boehnen Hulbert & Berghoff LLP

(57) ABSTRACT

The present invention relates to a pharmaceutical composition for preventing or treating a bone-related disease; and the pharmaceutical composition is very effective in preventing or treating bone-related diseases in that it not only promotes differentiation of preosteoblast cells into osteoblasts to induce production of mineralized nodules, but also, at the same time, inhibits differentiation of bone marrow cells into osteoclasts and the function of osteoclasts so that bone homeostasis is effectively regulated. In addition, the present invention relates to a pharmaceutical composition for preventing or treating a menopausal disease, in particular, a menopausal bone disease; and the pharmaceutical composition is very effective in preventing or treating a menopausal bone-related disease in that it not only increases the volume of trabecular bone and promotes differentiation of preosteoblast cells into osteoblasts to induce production of mineralized nodules, but also, at the same time, inhibits differentiation of bone marrow cells into osteoclasts and the function of osteoclasts so that bone homeostasis is effectively regulated.

5 Claims, 8 Drawing Sheets

[FIG. 1]

Formula 1

Tauroursodeoxycholic acid

Deoxycholic acid

Taurocholic acid

PHARMACEUTICAL COMPOSITION FOR TREATMENT OF BONE-RELATED DISEASE

CROSS-REFERENCE TO RELATED APPLICATIONS

This application is a U.S. National Stage application of International Patent Application PCT/KR2018/006174, filed May 30, 2018, which claims the benefit of priority of Korean Patent Applications nos. 10-2017-0068400, filed Jun. 1, 2017; 10-2018-0005406, filed Jan. 16, 2018; and 10-2018-0055737, filed May 16, 2018.

TECHNICAL FIELD

The present invention relates to a pharmaceutical composition for preventing or treating a bone-related disease.

BACKGROUND ART

Osteoporosis, a typical bone-related disease, is a disease caused by regulation imbalance in bone homeostasis between osteoclasts that resorb bone and osteoblasts that form bone, and refers to a skeletal disorder characterized by weakened bone strength which may lead to an increased risk of fracture (definition by National Institutes of Health (NIH), 2000).

The regulation imbalance in bone homeostasis may occur due to aging, systemic disease, menopause, or the like, and corresponds to a systemic disease in which bone density decreases and the microstructure of bone tissue degenerates, thereby leading to an increased risk of fracture. In other words, bone density is maintained while keeping a balance between destruction of old bones and creation of new bones. However, in a case where replacement by new bones is not achieved smoothly due to aging, menopause, or the like, bones become loose. As this process occurs repeatedly, bones become thinner, thereby leading to an increased risk of bone breakage or fracture.

In particular, the menopause means a phenomenon where ovulation and production of female hormones no longer occur due to decreased function of the ovary. It is known that the menopause is a phenomenon which occurs after the age of 40's as aging progresses; however, there is a tendency that early menopause increases even in young women under the age of 40. Women who have had their ovaries removed are more vulnerable to a menopause-related disease. Dysfunction of the hypothalamic-pituitary-ovary gonadal axis caused by decreased function of the ovary results in physical and mental changes such as changes in sex hormones, lipid and cardiovascular metabolism, bone metabolism, and memory. Menopausal women are at risk of many diseases due to hormonal imbalance, calcium deficiency, and increased oxidative stress in the body. In other words, estrogen changes in menopause dramatically increase the incidence of diseases such as coronary artery disease, osteoporosis, and Alzheimer's disease. In particular, a decrease in estrogen after menopause causes rapid bone loss. Accordingly, in order to improve physical and mental health of menopausal women, and their quality of life, it has been required to develop a therapeutic agent that can improve menopausal symptoms, and drugs such as hormone replacement therapy and non-steroidal agents have been developed to improve such menopausal diseases. However, most of these drugs are known to have adverse effects such as headache and weight gain. In particular, even in a case of estrogen replacement therapy, since hormones are artificially administered into the body, there is not only a rejection reaction thereto, but also an increased risk of uterine bleeding, stroke, heart attack, breast cancer, and uterine cancer (Swaran L., et. al., Obstetrics & Gynecology, 91, 678-684, 1998). Therefore, there is a need to develop a new therapeutic agent for menopausal diseases, which has excellent effects that can alleviate symptoms of menopausal diseases without adverse effects.

Osteoporosis is a disease in which bone mass, that is, bone density, required to maintain normal activity is decreased, for example, due to a decrease in bone calcium content, and thus fracture is easily caused even by a light impact. The state before progressing to osteoporosis is called osteopenia, which means a state until holes are created as bone thickness or the like gradually becomes thinner and lighter. In addition, osteomalacia refers to a condition in which calcium is not mixed with bone, and thus the bone bends in a state where cartilage is formed, in a case where vitamin D is deficient or in a case where there is a kidney disease in which calcium is excreted in large quantities. In addition, bone atrophy refers to a condition caused by degenerative reduction of bone, that is, decrease in bone mass of bone tissue that has already been completed.

Since the amount of bone in the human body is maintained through regulation of bone homeostasis achieved by the balance between osteoblasts and osteoclasts, it is important to develop a therapeutic agent which targets molecules that play an important role in these cells. That is, in a case where activity of osteoblasts that form bone decreases and activity of osteoclasts that resorb bone increases, breakdown of bones is promoted, leading to diseases such as osteoporosis in which bones become thinner and easily broken; and therefore, proteins that can regulate activity of osteoblasts and osteoclasts are studied as therapeutic agents for bone diseases (Gregory R. Mundy, Journal of Bone and Mineral Metabolism (1996) 14:59-64; Chad Deal, nature clinical practice RHEUMATOLOGY (2009) vol 5 no 1; Kalervo Vaananen, Advanced Drug Delivery Reviews 57 (2005) 959-971). However, currently available drugs for treating osteoporosis, except parathyroid hormone, are mostly drugs that inhibit activity of osteoclasts, and thus there is an urgent need to develop drugs that target osteoblasts.

Meanwhile, cholesterol sulphate, which corresponds to sterol sulphate, is one of the components constituting the cell membrane, and is present at a high concentration in blood, skin, and the like. However, for the cholesterol sulphate, until now, only some of its functions associated with immune function and differentiation into skin cells have been identified, and there has been no clear report on its in vivo role.

DISCLOSURE

Technical Problem

The present invention has been made to solve the above-mentioned conventional problems, and provides a pharmaceutical composition for preventing or treating a bone-related disease, or a food composition, the composition comprising sterol sulphate as an active ingredient.

For the purpose of the present invention, in order to prevent or treat a bone-related disease, there is proposed a method for further supplying sterol sulphate or for inhibiting decomposition of sterol sulphate, so that a high concentration of sterol sulphate is maintained in the body. For the method for further supplying sterol sulphate, there is provided a compound of Formula 1 of the present invention ([(3S,8S,9S,10R,13R,14S,17R)-10,13-dimethyl-17-[(2R)-6-methylheptan-2-yl]-2,3,4,7,8,9,11,12,14,15,16,17-dodecahydro-1H-cyclopenta[a]phenanthren-3-yl] hydrogen sulphate). For the method for inhibiting decomposition of sterol sulphate, there is provided a compound of Formula 2 of the present invention (6-oxo-6,7,8,9,10,11-hexahydrocyclohepta[c]chromen-3-yl sulfamate).

However, the technical problem to be solved by the present invention is not limited to the above-mentioned problems, and other problems which are not mentioned will be clearly understood by those skilled in the art from the following description. cl Technical Solution Hereinafter, various embodiments described herein are described with reference to the drawings. In the following description, for a complete understanding of the present invention, various specific details are set forth, such as specific configurations, compositions, and processes. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in association with the embodiment is included in one or more embodiments of the present invention. Thus, the circumstances in "one embodiment" or "an embodiment" at various places throughout the present specification do not necessarily represent the same embodiment of the present invention. Additionally, particular features, configurations, compositions, or characteristics may be combined in any suitable manner in one or more embodiments.

In view of the fact that no report has been made on a drug that simultaneously exerts effects of increasing bone formation caused by osteoblasts and inhibiting bone resorption caused by osteoclasts, the present inventors have repeatedly conducted research on such a compound. As a result, the present inventors have found that sterol sulphate, in particular, [(3S,8S,9S,10R,13R,14S,17R)-10,13-dimethyl-17-[(2R)-6-methylheptan-2-yl]-2,3,4,7,8,9,11,12,14,15,16,17-dodecahydro-1H-cyclopenta[a]phenanthren-3-yl] hydrogen sulphate exhibits a remarkable effect, through a process of regulating bone homeostasis, on treatment and prevention of a bone-related disease, and thus have completed the present invention.

In an embodiment of the present invention, there is provided a pharmaceutical composition for preventing or treating a bone-related disease, comprising sterol sulphate as an active ingredient.

In the present invention, the sterol is short for steroid alcohol and refers to an organic molecule of steroid compound. It is reported that the sterol can be found in most plants, animals, and fungi, and can play important physiological functions in eukaryotic organisms, such as constituting the membrane of animal cells or affecting fluidity thereof, and acting as a secondary signal transducer. For the purpose of the present invention, the sterol may include sulphates of campesterol, which is vegetable sterol, sitosterol, stigmasterol, and cholesterol which is animal sterol. The sterol sulphate is preferably cholesterol sulphate, which may be, but is not limited to, [(3S,8S,9S,10R,13R,14S,17R)-10,13-dimethyl-17-[(2R)-6-methylheptan-2-yl]-2,3,4,7,8,9,11,12,14,15,16,17-dodecahydro-1H-cyclopenta[a]phenanthren-3-yl] hydrogen sulphate, a compound represented by Formula 1:

[Formula 1]

In another embodiment of the present invention, there is provided a pharmaceutical composition for preventing or treating a bone-related disease, comprising, as an active ingredient, [(3S,8S,9S,10R,13R,14S,17R)-10,13-dimethyl-17-[(2R)-6-methylheptan-2-yl]-2,3,4,7,8,9,11,12,14,15,16,17-dodecahydro-1H-cyclopenta[a]phenanthren-3-yl] hydrogen sulphate.

Here, in the present invention, the compound represented by Formula 1 is present at the same concentration as dehydroepiandrosterone sulphate (DHEAS), which is steroid sulphate circulating in the human body; and the compound is a component constituting the cell membrane and protects red blood cells from osmotic lysis, is a component that regulates a sperm receptor, and also regulates activity associated with cell signal transduction, blood coagulation, fibrin lysis, and epidermal cell adhesion (J Lipid Res. 2003 July; 44 (7): 1268-78).

In the present invention, the bone-related disease may be caused by a loss of harmony, in terms of activity, between osteoblasts, which play a role of producing bone in the body, and osteoclasts, which play a role of destroying bone in the body.

In the present invention, the osteoclasts are large multinuclear cells which destroy or resorb bone tissue that becomes unnecessary in the course of bone growth. Mature osteoclasts are multinuclear cells, and are formed by originating from hematopoietic stem cells and differentiation therefrom. In addition, osteoblasts differentiated from mesenchymal stem cells survive for about 34 months and form new bones at sites where activated osteoclasts have decomposed old bones. Bone formation is completed through a process in which numerous osteoblasts make bone matrix and the matrix becomes mineralized. After such bone formation is completed, about 70% or more of osteoblasts become dead and some of them survive by being differentiated into osteocytes and bone lining cells. However, in a case where such homeostasis is constantly imbalanced, a bone-related disease may occur.

Therefore, for the purpose of the present invention, a pharmaceutical composition comprising the sterol sulphate as an active ingredient can simultaneously play a role of promoting differentiation into osteoblasts and a role of inhibiting differentiation into osteoclasts and the function thereof, unlike previously reported pharmaceutical compositions for a bone-related disease. Thus, such a pharmaceutical composition is more effective in treatment of a bone-related disease.

Specifically, in the present invention, the bone-related disease may be at least one selected from the group consisting of osteoporosis, osteomalacia, osteopenia, bone atrophy, fibrous dysplasia, Paget's disease, hypercalcemia, neoplastic destruction of bone, cancer-related bone resorption diseases, fracture, osteolysis, osteoarthritis, and rheumatoid arthritis.

Here, in the present invention, the osteoporosis may be at least one selected from the group consisting of primary osteoporosis due to aging, primary osteoporosis due to menopause, primary osteoporosis due to ovarian extraction, and primary osteoporosis due to testicular removal. In addition, the osteoporosis may be at least one selected from the group consisting of glucocorticoid-induced osteoporosis, osteoporosis associated with hyperthyroidism, fixation-induced osteoporosis, heparin-induced osteoporosis, immunosuppression-induced osteoporosis, osteoporosis due to renal insufficiency, inflammatory osteoporosis, osteoporosis due to Cushing's syndrome, rheumatic osteoporosis, and osteoporosis due to estrogen synthesis inhibitor.

In addition, the present invention provides a pharmaceutical composition for preventing or treating a menopausal disease, comprising, as an active ingredient, a compound represented by Formula 2.

[Formula 2]

In an embodiment of the present invention, the compound of Formula 2 is 6-oxo-6,7,8,9,10,11-hexahydrocyclohepta[c]chromen-3-yl sulfamate, which is one of steroid sulfatase (STS) inhibitors. This compound inhibits conversion of cholesterol sulphate (steroid sulphate), which is a substrate of steroid sulfatase, into cholesterol, thereby increasing the concentration of cholesterol sulphate in blood. Thus, such a compound may be effectively used for preventing, improving, and treating a menopause-related disease. Other steroid sulfatase inhibitors include AHBS ($C_6H_7NO_4S$), Danazol ($C_{22}H_{27}NO_2$), EMATE ($C_{18}H_{23}NO_4S$), Irosustat ($C_{14}H_{15}NO_5S$), KW-2581 ($C_{25}H_{36}N_2O_4S$), Progesterone ($C_{21}H_{30}O_2$), SR-16157 ($C_{28}H_{46}N_2O_4S$), STX213 ($C_{28}H_{146}N_2O_4S$), and STX681 ($C_{16}H_{13}BrN_6O_3S$), and the like. Any substance may be included therein without limitation as long as the substance is capable of inhibiting steroid sulfatase.

Meanwhile, cholesterol sulphate is one of the components constituting the cell membrane, and is present at a high concentration in blood, skin, and the like. However, for the cholesterol sulphate, until now, only some of its functions associated with immune function and differentiation into skin cells have been identified.

In an embodiment of the present invention, the menopausal disease is a menopausal bone disease, and the bone disease may be at least one selected from the group consisting of type I osteoporosis due to menopause, type I osteoporosis due to ovarian extraction, spinal stenosis, spinal compression fracture, and osteoarthritis.

In particular, osteoporosis is a typical bone-related disease and is a disease in which bone density decreases due to regulation imbalance in bone homeostasis between osteoblasts that form bone and osteoclasts that resorb bone; and osteoporosis refers to a skeletal disorder characterized by weakened bone strength which may lead to an increased risk of fracture.

In general, the regulation imbalance in bone homeostasis may occur due to aging, systemic disease, menopause, or the like, and corresponds to a systemic disease in which bone density decreases and the microstructure of bone tissue degenerates, thereby leading to an increased risk of fracture. In other words, bone density is maintained while keeping a balance between destruction of old bones and creation of new bones. However, in a case where replacement by new bones is not achieved smoothly due to various causes, bones become loose. As this process occurs repeatedly, bones become thinner, thereby leading to an increased risk of bone breakage or fracture.

According to the American Academy of Orthopedic Surgeons, depending on the cause, osteoporosis is divided into primary osteoporosis, which occurs in adults in the absence of other systemic diseases that may cause osteoporosis, and secondary osteoporosis with other obvious causative diseases. Primary osteoporosis is further subdivided into postmenopausal osteoporosis (type I osteoporosis), age-associated osteoporosis or senile osteoporosis (type II osteoporosis), idiopathic osteoporosis, and the like (American Academy of Orthopaedic Surgeons. "Osteoporosis/Bone health in adults as a national public health priority." Position Statement 1113 (2015)).

In particular, type I osteoporosis may occur even in young female patients under the age of 40 due to early menopause; and in a case where such early menopause occurs, those patients are known to exhibit remarkably decreased bone density as compared with patients who normally develop menopause after the age of 50 (Shuster, Lynne T., et al. "Premature menopause or early menopause: long-term health consequences." Maturitas 65.2 (2010): 161-166).

In an embodiment of the present invention, the composition according to the present invention may increase the volume of trabecular bone. The trabecular bone refers to the tissue that has a spongy honeycomb-like structure and constitutes an inner layer of bone.

In particular, in type I osteoporosis, bone turnover increases due to a decrease in hormones such as estrogen and androgen after menopause, and bone resorption outpaces bone formation, resulting in a decrease in bone density. Type I osteoporosis is characterized in that a relatively greater loss is observed in trabecular bone than in cortical bone. In contrast, type II osteoporosis is associated with a gradual decrease in bone density with aging in both men and women, and the main cause thereof is a decrease in stem cells for bone formation. Type II osteoporosis is characterized in that a loss is observed mainly in cortical bone (Dobbs, Matthew B., Joseph Buckwalter, and Charles Saltzman. "Osteoporosis: the increasing role of the orthopaedist." The Iowa orthopaedic journal 19 (1999): 43).

In an embodiment of the present invention, the pharmaceutical composition according to the present invention provides a pharmaceutical composition for preventing or treating a menopausal disease, in which the pharmaceutical composition promotes differentiation of preosteoblast cells into osteoblasts.

In addition, in an embodiment of the present invention, the pharmaceutical composition according to the present invention provides a pharmaceutical composition for preventing or treating a menopausal disease, in which the pharmaceutical composition inhibits differentiation of bone marrow cells into osteoclasts.

In the present invention, a menopausal bone-related disease may be caused by a loss of harmony, in terms of activity, between osteoblasts, which play a role of producing bone in the body, and osteoclasts, which play a role of destroying bone in the body.

In the present invention, the osteoclasts are large multinuclear cells which destroy or resorb bone tissue that becomes unnecessary in the course of bone growth. Mature osteoclasts are multinuclear cells, and are formed by originating from hematopoietic stem cells and differentiation therefrom. In addition, osteoblasts differentiated from mesenchymal stem cells survive for about 34 months and form new bones at sites where activated osteoclasts have decomposed old bones. Bone formation is completed through a process in which numerous osteoblasts make bone matrix and the matrix becomes mineralized. After such bone formation is completed, about 70% or more of osteoblasts become dead and some of them survive by being differentiated into osteocytes and bone lining cells. However, in a case where such homeostasis is constantly imbalanced, a bone-related disease may occur.

The pharmaceutical composition according to the present invention not only can increase the volume of trabecular bone, but also can simultaneously play a role of promoting differentiation into osteoblasts and a role of inhibiting differentiation into osteoclasts and the function thereof. Thus, such a pharmaceutical composition is more effective in treatment of a menopausal disease, in particular, a menopausal bone disease.

Meanwhile, in the present invention, the "prevention" may include, without limitation, any act of blocking symptoms caused by bone-related diseases, blocking symptoms caused by menopausal diseases, or suppressing or delaying the symptoms, using the pharmaceutical composition of the present invention.

In addition, in the present invention, the "treatment" may include, without limitation, any act of ameliorating or beneficially altering symptoms caused by bone-related diseases or symptoms caused by menopausal diseases, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

In the present invention, the pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a fragrance, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

As used herein, the term "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 10 g/kg or 0.001 to 10 mg/kg, per day. Administration may be made once a day or several times a day. The dose is not intended to limit the scope of the present invention in any way. The pharmaceutical composition according to the present invention may be formulated in the form of pills, sugar-coated tablets, capsules, liquids, gels, syrups, slurries, or suspensions.

In other embodiments of the present invention, there are provided a food composition for preventing or improving a bone-related disease, comprising, as an active ingredient, the compound represented by Formula 1, and a food composition for preventing or improving a menopausal disease, comprising, as an active ingredient, the compound represented by Formula 2.

Meanwhile, in the present invention, "improvement" may include, without limitation, any act of ameliorating or beneficially altering symptoms caused by bone-related diseases, using the food composition of the present invention.

The food composition comprising, as an active ingredient, the compound of the present invention may be prepared in the form of various foods, for example, beverages, gums, teas, vitamin complexes, powders, granules, tablets, capsules, confectionery, rice cakes, and bread.

In the present invention, when the compound is included in the food composition, the compound may be added in an amount corresponding to a ratio of 0.1% to 50% of the total weight. However, the amount of the compound is not limited thereto.

In the present invention, in a case where the food composition is prepared in the form of beverages, there is no particular limitation except that the food composition is contained at an indicated proportion. In such a case, various flavors, natural carbohydrates, or the like may be included as additional ingredients as in ordinary beverages. Specifically, examples of the natural carbohydrate may include monosaccharides such as glucose, disaccharides such as fructose, polysaccharides such as sucrose, conventional sugars such as dextrin and cyclodextrin, sugar alcohols such as xylitol, sorbitol, and erythritol. Examples of the flavor may include natural flavors (thaumatin, stevia extracts, such as rebaudioside A, glycyrrhizin, and the like), and synthetic flavors (saccharin, aspartame, and the like).

In the present invention, in addition to the above-mentioned ingredients, the food composition of the present invention may contain various nutrients, vitamins, minerals (electrolytes), flavoring agents such as synthetic flavoring agents and natural flavoring agents, colorants, pectic acid and salts thereof, alginic acid and salts thereof, organic acids, protective colloidal thickeners, pH adjusting agents, stabilizers, preservatives, glycerin, alcohol, carbonizing agents as used in carbonated beverages, and the like.

In the present invention, the above-mentioned ingredients may be used independently or in combination. Although proportions of the additives do not correspond to essential elements of the present invention, such additives may be selected in a range of 0.1 to about 50 parts by weight per 100 parts by weight of the food composition of the present invention. However, the amount of such additives is not limited thereto.

Advantageous Effects

The pharmaceutical composition and the food composition, each of which comprises, as an active ingredient, the compound of Formula 1 according to the present invention, are very effective in preventing or treating a bone-related disease in that these compositions not only promote differentiation of preosteoblast cells into osteoblasts to induce production of mineralized nodules, but also, at the same time, inhibit differentiation of bone marrow cells into osteoclasts and the function of osteoclasts so that bone homeostasis is effectively regulated.

In addition, the pharmaceutical composition and the food composition, each of which comprises, as an active ingredient, the compound of Formula 2 according to the present invention, are very effective in preventing, improving, or treating a menopausal disease, in particular, a menopausal bone-related disease, in that these compositions not only increase the volume of trabecular bone, increase the concentration of cholesterol sulphate in blood, and promote differentiation of preosteoblast cells into osteoblasts to induce production of mineralized nodules, but also, at the same time, have an effect of inhibiting differentiation of bone marrow cells into osteoclasts and the function of osteoclasts so that bone homeostasis is effectively regulated.

BEST MODE

It has been checked whether the compound according to the present invention remarkably promotes osteoblast mineralized nodules. As a result, in the preosteoblast cells to which the compound of Formula 1 that is the compound of the present invention has been added, the amount of pigments colored in the nodules increases as the treatment concentration increases from 15 μM to 35 μM, as compared with a negative control group (0 μM) which has not been treated with the compound. However, for the preosteoblast cells to which tauroursodeoxycholic acid, deoxycholic acid, or taurocholic acid, which is classified as a compound derived from bile acid similar to the compound of Formula 1, has been added, these acids are found to have no effect on the differentiation of preosteoblast cells at all concentrations applied in the experiment.

In addition, as a result of experiments conducted in an ovary-extracted mouse model, it is identifiable that the OVX group exhibits an about 40% decrease in the volume of trabecular bone as compared with the control group. On the contrary, the group having orally received the compound of Formula 2 exhibits a 90% increase in the volume of trabecular bone as compared with the OVX group having orally received a vehicle only. In other words, this suggests that the compound of Formula 2 effectively treats type I osteoporosis induced by ovarian extraction.

Mode for Invention

Hereinafter, the present invention will be described in more detail by way of examples. These examples are only for describing the present invention in more detail, and it will be apparent to those skilled in the art that according to the gist of the present invention, the scope of the present invention is not limited by these examples.

Example 1. Identification of Prophylactic or Therapeutic Effect of Compound of Formula 1 on Bone-Related Diseases

Example 1-1. Isolation of Preosteoblast Cells and Bone Marrow Cells

In order to identify a regulatory effect of a compound according to the present invention on bone homeostasis, preosteoblast cells and bone marrow cells were isolated from mice.

In order to isolate preosteoblast cells, the calvarium was removed from 1- to 3-day-old mice, and then preosteoblast cells were obtained via a process in which the calvarium was subjected to treatment with 1 mg/ml collagenase and 2 mg/ml dispase.

In addition, in order to isolate bone marrow cells, the tibia and the femur were removed from 4- to 6-week-old male mice, and then bone marrow cells were obtained via a process in which both ends of the bones were cut and the cells were extracted from the middle part.

Example 1-2. Measurement of Osteoblast Mineralized Nodules

It was checked whether the compound according to the present invention remarkably promotes osteoblast mineralized nodules.

Figure 1:
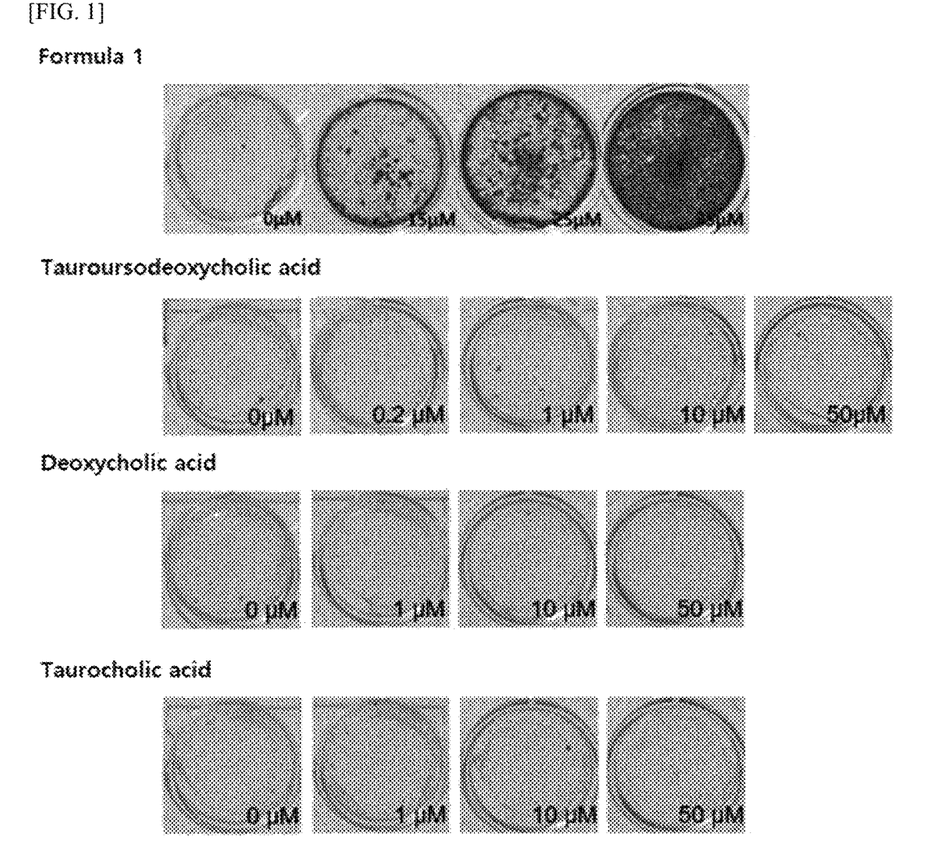
FIG. 1 illustrates results obtained by identifying the degree of mineralized nodule production of osteoblasts caused by addition of the compound of Formula 1, tauroursodeoxycholic acid, deoxycholic acid, or taurocholic acid, according to an embodiment of the present invention.

The preosteoblast cells obtained in Example 1-1 were dispensed into a 12-well cell culture plate at $0.5 \times 10^5$ cells/well, and were induced to differentiate into osteoblasts by adding, to α-MEM medium supplemented with fetal bovine serum (FBS), which corresponds to 10% of the medium volume, antibiotics (penicillin-streptomycin), which correspond to 1% of the medium volume, 50 μg/ml L-ascorbic acid, and 10 mM β-glycerophosphate, the compound of Formula 1, which is a compound of the present invention, or tauroursodeoxycholic acid, deoxycholic acid, or taurocholic acid, which is a compound derived from bile acid similar to the compound of Formula 1 of the present invention, at concentrations of 0 to 50 μM, respectively. Here, the medium for differentiation induction was replaced with fresh medium at 2- to 3-day intervals, and differentiation induction was performed for a total of 21 days. In order to identify the differentiation into osteoblasts, alizarin red staining was performed. Differentiation-induced cells were fixed by being incubated with 10% neutral formalin at 4° C. for 20 minutes, and then stained by being incubated with 1.36% alizarin red solution (pH 4.1 to 4.3) for 40 minutes. The results are illustrated in FIG. 1. According to the experimental results, in the preosteoblast cells to which the compound of the present invention had been added, the amount of pigments colored in the nodules increased as the treatment concentration increases from 15 μM to 35 μM, as compared with a negative control group (0 μM) which had not been treated with the compound. However, for the preosteoblast cells to which tauroursodeoxycholic acid, deoxycholic acid, or taurocholic acid, which is classified as a compound derived from bile acid similar to the compound of Formula 1, had been added, these acids were found to have no effect on the differentiation of preosteoblast cells at all concentrations applied in the experiment. This means that among the compounds derived from bile acid, only the compound of Formula 1 of the present invention has a specific effect on the differentiation into osteoblasts.

Figure 2:
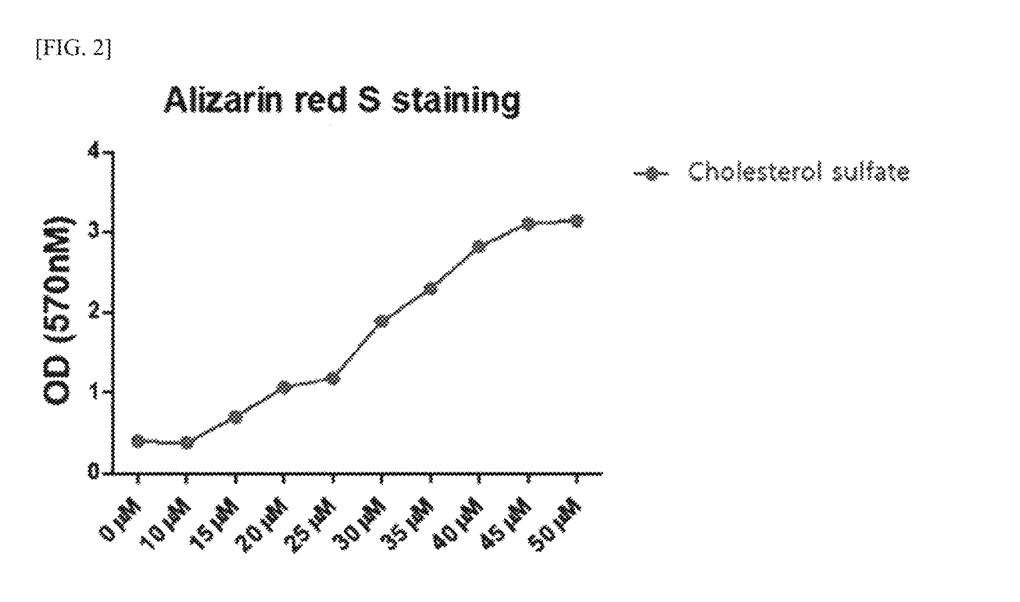
FIG. 2 illustrates results obtained by identifying the degree of mineralized nodule production of osteoblasts caused by addition of the compound of Formula 1, according to an embodiment of the present invention.

In order to quantitatively evaluate the degree of differentiation of preosteoblast cells to which the compound of Formula 1 had been added, the pigments colored in the nodules were extracted with 10% cetylpyridinium chloride, and then the absorbance was measured at 570 nm. The results are illustrated in FIG. 2. According to the experimental results, the OD value was measured as about 0.5 at 10 μM, whereas the OD value was measured as 2 at 35 μM and as about 3 at 40 μM. From these results, it was found that an effect of the compound on the differentiation into osteoblasts increases in a range of 10 to 45 μM in a concentration-dependent manner.

Figure 3:
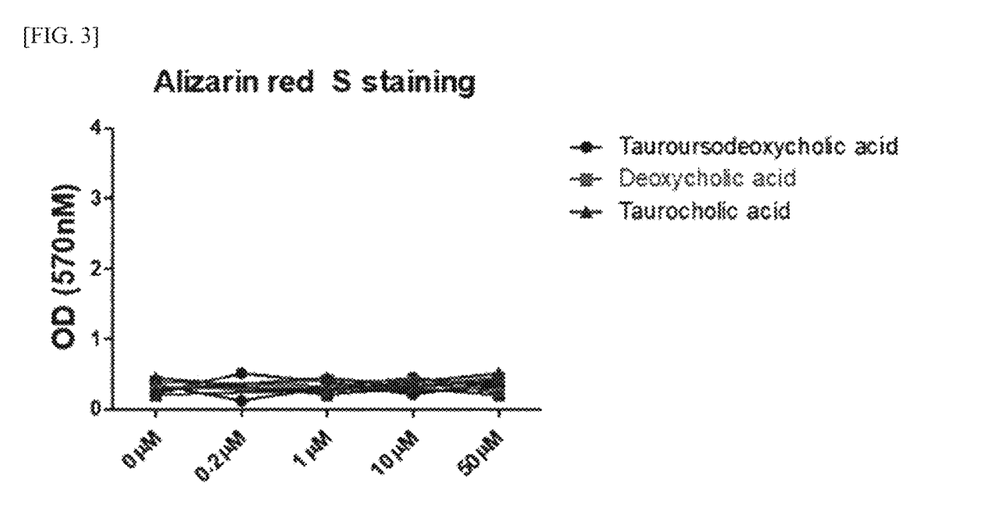
FIG. 3 illustrates results obtained by identifying the degree of mineralized nodule production of osteoblasts caused by addition of tauroursodeoxycholic acid, deoxycholic acid, or taurocholic acid, according to an embodiment of the present invention.

The results obtained by performing quantification with tauroursodeoxycholic acid, deoxycholic acid, or taurocholic acid are illustrated in FIG. 3. Consistent with the images in FIG. 1, these acids showed no significant difference even in quantitative terms as compared with a negative control group (0 μM).

Example 1-3. Measurement of Differentiation into Osteoblasts

In order to identify whether the compound according to the present invention promotes differentiation of preosteoblast cells into osteoblasts, expression of osteoblast differentiation marker genes was checked.

In Example 1-2, the preosteoblast cells were subjected to treatment with 25 μM of [(3S,8S,9S,10R,13R,14S,17R)-10, 13-dimethyl-17-[(2R)-6-methylheptan-2-yl]-2,3,4,7,8,9,11, 12,14,15,16,17-dodecahydro-1H-cyclopenta[a] phenanthren-3-yl] hydrogen sulphate, and induced to differentiate by being incubated for 15 days. Each total RNA was extracted therefrom using RNeasy Mini Kit (Qiagen) according to the protocol provided in the kit. 2 μg of the extracted RNA was reacted with RevertAid Revert Transcriptase (Thermo Scientific, USA) for 1 hour at 42° C. to obtain cDNA, and then cDNA was subjected to real-time PCR using SensiFAST™ SYBR Hi-ROX Kit (Bioline). Specific reaction conditions were 3-minute denaturation at 95° C., followed by 40 cycles of 5 seconds at 95° C., 10 seconds at 60° C., and 15 seconds at 72° C. The quantitative results thus obtained are illustrated in FIG. 4.

Figure 4:
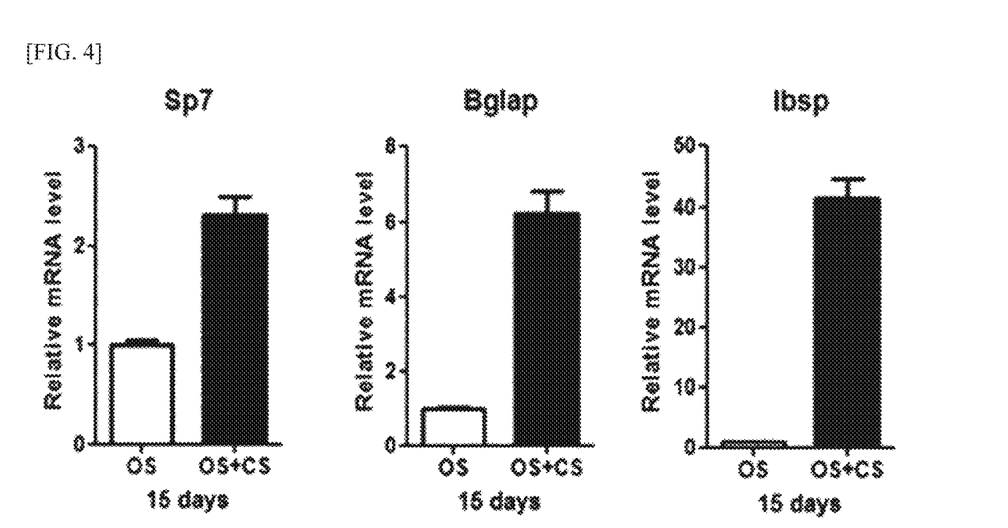
FIG. 4 illustrates results obtained by identifying the expression of osteoblast differentiation marker genes, according to an embodiment of the present invention.

As illustrated in FIG. 4, gene expression of Sp7, Bgiap, and Ibsp, which are genes corresponding to osteoblast differentiation markers, showed a remarkable 2-fold or higher difference as compared with a control group (OS).

From the above results, it can be seen that the compound according to the present invention not only remarkably increases the number of mineralized nodules produced in osteoblasts, but also promotes differentiation of preosteoblast cells into osteoblasts.

Example 1-4. Measurement of Differentiation into Osteoclasts

It was identified whether the compound according to the present invention remarkably inhibits differentiation into osteoclasts.

The bone marrow cells obtained in Example 1-1 were dispensed into a 96-well cell culture plate at $0.5 \times 10^4$ cells/well, and were induced to differentiate into osteoclasts by adding, to α-MEM medium supplemented with fetal bovine serum (FBS), which corresponds to 10% of the medium volume, antibiotics (penicillin-streptomycin), which correspond to 1% of the medium volume, 30 ng/ml M-CSF, and 50 ng/ml RANKL, [(3S,8S,9S,10R,13R,14S,17R)-10,13-di-methyl-17-[(2R)-6-methylheptan-2-yl]-2,3,4,7,8,9,11,12, 14,15,16,17-dodecahydro-1H-cyclopenta[a]phenanthren-3-yl] hydrogen sulphate at concentrations of 0 to 25 μM, respectively. Here, the medium for differentiation induction was replaced with fresh medium at 2-day intervals, and differentiation induction was performed for a total of 4 to 5 days.

Figure 5:
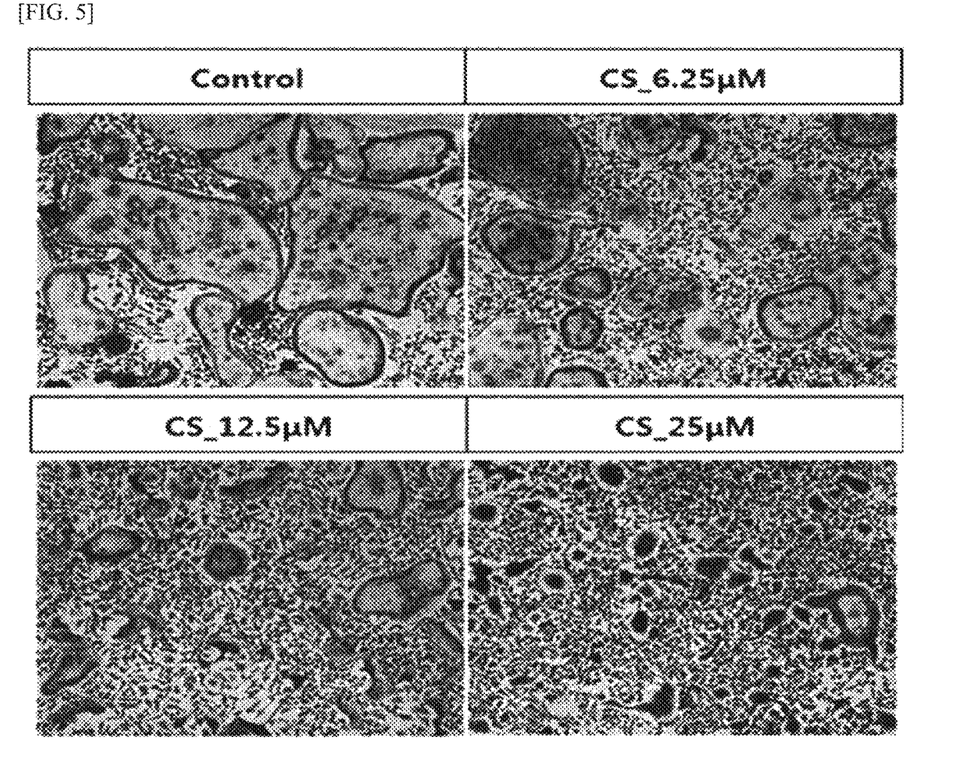
FIG. 5 illustrates results obtained by identifying the degree of differentiation of bone marrow cells into osteoclasts, according to an embodiment of the present invention.

In order to identify the degree of differentiation of the differentiated bone marrow cells, the cells were subjected to staining using TRAP staining kit (Sigma Aldrich, USA) according to the protocol provided by the manufacturer, and measurement was performed using a microscope. The results are illustrated in FIG. 5. The results obtained by measuring TRAP enzyme activity are illustrated in FIG. 6.

Figure 6:
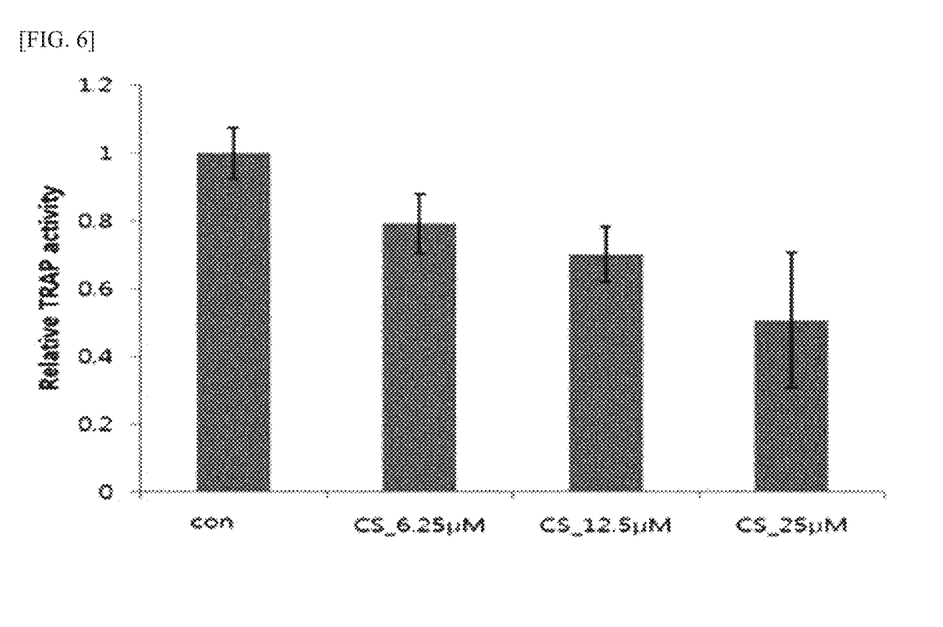
FIG. 6 illustrates results obtained by evaluating the function of osteoclasts, according to an embodiment of the present invention.

As illustrated in FIGS. 5 and 6, the compound according to the present invention inhibited differentiation of bone marrow cells into osteoclasts, and the compound according to the present invention exhibited osteoclast function inhibition of about 0.2 at concentrations of 6.25 µM and 12.5 µM, and osteoclast function inhibition of about 0.3 at a concentration of 25 µM, as compared with a negative control group.

From the above results, it can be seen that [(3S,8S,9S,10R,13R,14S,17R)-10,13-dimethyl-17-[(2R)-6-methylheptan-2-yl]-2,3,4,7,8,9,11,12,14,15,16,17-dodecahydro-1H-cyclopenta[a]phenanthren-3-yl] hydrogen sulphate according to the present invention not only inhibits the differentiation of bone marrow cells into osteoclasts, but also inhibits the function of osteoclasts.

Example 2. Identification of Prophylactic or Therapeutic Effect of Compound of Formula 2 on Bone-Related Diseases

Example 2-1. Drug Administration Experiment in Ovary-Extracted Mouse Model

Twenty-four 8-week-old C57BL/6 female mice were randomly divided into three groups, that is, control group (sham), ovary-extracted group (OVX), and OVX+Formula 2 group obtained by administering the compound of Formula 2 to the ovary-extracted group, each group consisting of 8 mice. All three groups were anesthetized using zoletil and rompun. Then, the OVX and OVX+Formula 2 groups were subjected to ovary extraction, and then sutured. The control group was subjected to ovary exposure, and then sutured without ovarian removal. Osteoporosis was induced for 4 weeks.

[Formula 2]

Starting from 4 weeks after ovarian extraction, on five days a week and once a day, the control group and the OVX group orally received 200 µl of vehicle (tetrahydrofuran:PEG-400:water=1:6:3 in volume), and the OVX+Formula 2 group orally received 200 µl obtained by mixing 5 mg/kg of compound of Formula 2 with a vehicle.

After oral administration for 4 weeks, all mice were sacrificed and the femur was extracted therefrom. The extracted femur was fixed in 10% neutral formalin. Photographs were taken at 7.1 µm voxel size using Skyscan 1173 micro-CT machine, and then bone density was analyzed by CTAn program. The results are illustrated in FIG. 7.

Figure 7:
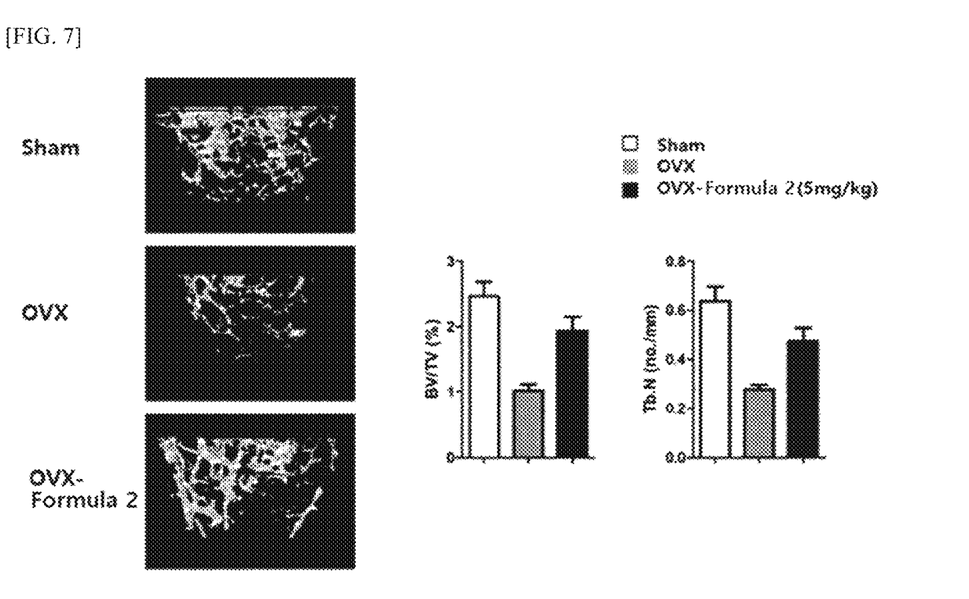
FIG. 7 illustrates results obtained by analyzing the bone density in an ovary-extracted mouse model, according to an embodiment of the present invention.

As illustrated in FIG. 7, it is identifiable that the OVX group exhibits an about 40% decrease in the volume of trabecular bone as compared with the control group. On the contrary, the group having orally received the compound of Formula 2 exhibited a 90% increase in the volume of trabecular bone as compared with the OVX group having orally received the vehicle only. In other words, this suggests that the compound of Formula 2 effectively treats type I osteoporosis induced by ovarian extraction.

Example 2-2. Differentiation Experiment into Osteoblasts

The calvarium was removed from 1- to 3-day-old mice, and then subjected to enzymatic treatment with 1 mg/ml collagenase and 2 mg/ml dispase, to obtain preosteoblast cells. The obtained preosteoblast cells were dispensed into a 12-well culture plate ($0.5 \times 10^5$ cells/well), and divided into a group with α-MEM (10% FBS, 1% penicillin/streptomycin, 50 µg/ml L-ascorbic acid, 10 mM β-glycerophosphate) supplemented with 0 to 50 µM of cholesterol sulphate alone, and a group with α-MEM supplemented with 0 to 50 µM of cholesterol sulphate and further treated with 5 µM of compound of Formula 2. Then, differentiation into osteoblasts was induced. Replacement of the medium for differentiation was performed at 2- to 3-day intervals and differentiation was induced for a total of 14 to 21 days.

Alizarin red S staining was used to evaluate the differentiation into osteoblasts, thereby quantitatively evaluate the degree of mineralized nodule production. The differentiated cells were fixed in 10% neutral formalin at 4° C. for 20 minutes, and then stained with 1.36% alizarin red solution (pH 4.1 to 4.3) for 40 minutes. The stained pattern was photographed or scanned. The pigments colored in the nodules were extracted with 10% cetylpyridinium chloride for quantitative evaluation, and the absorbance was measured at 570 nm with a spectrophotometer. The degree of differentiation into osteoblasts is illustrated in FIG. 8.

Figure 8:
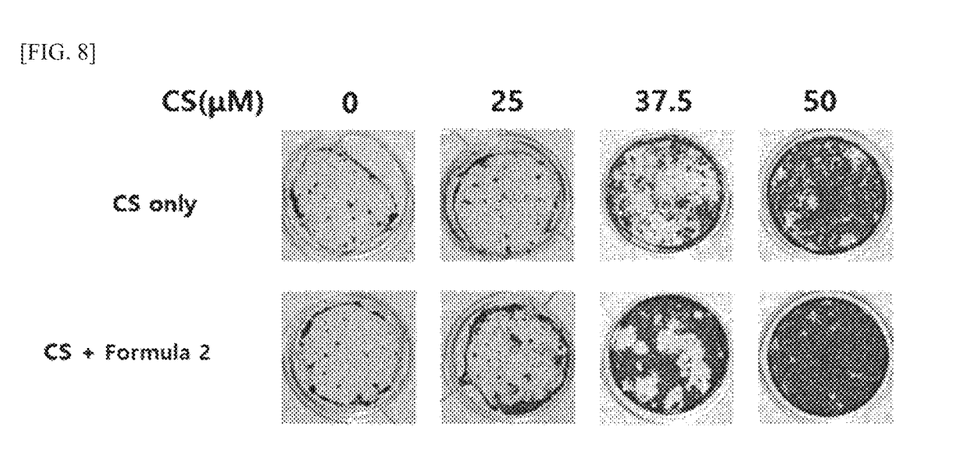
FIG. 8 illustrates results obtained by identifying the degree of differentiation into osteoblasts, according to an embodiment of the present invention.

As illustrated in FIG. 8, it is identifiable that cholesterol sulphate increases the differentiation into osteoblasts in a dose-dependent manner. On the contrary, it is identifiable that the differentiation into osteoblasts does not increase in a case where preosteoblast cells are treated with 6-oxo-6,7,8,9,10,11-hexahydrocyclohepta[c]chromen-3-yl sulfamate alone, whereas 6-oxo-6,7,8,9,10,11-hexahydrocyclohepta[c]chromen-3-yl sulfamate further enhances an effect of cholesterol sulphate in a case of being used in combination with cholesterol sulphate. This indicates that 6-oxo-6,7,8,9,10,11-hexahydrocyclohepta[c]chromen-3-yl sulfamate inhibits activity of the enzyme, steroid sulfatase, in osteoblasts, and thus increases the effective concentration of cholesterol sulphate in the osteoblasts, so that efficacy of cholesterol sulphate is increased by addition of 6-oxo-6,7,8,9,10,11-hexahydrocyclohepta[c]chromen-3-yl sulfamate.

From the above results, it is identifiable that 6-oxo-6,7,8,9,10,11-hexahydrocyclohepta[c]chromen-3-yl sulfamate is used to effectively treat type I osteoporosis, which is postmenopausal osteoporosis induced by ovarian extraction, because 6-oxo-6,7,8,9,10,11-hexahydrocyclohepta[c]chromen-3-yl sulfamate inhibits the enzyme, steroid sulfatase, to increase the effective concentration of cholesterol sulphate; and 6-oxo-6,7,8,9,10,11-hexahydrocyclohepta[c]

chromen-3-yl sulfamate promotes the differentiation into osteoblasts through a synergistic effect with cholesterol sulphate present in blood.

Although the present invention has been described in detail above, the scope of the present invention is not limited thereto. It will be obvious to those skilled in the art that various modifications and changes can be made without departing from the technical spirit of the present invention described in the claims.

INDUSTRIAL APPLICABILITY

The present invention relates to a pharmaceutical composition for preventing or treating a bone-related disease; and the pharmaceutical composition is very effective in preventing or treating bone-related diseases in that it not only promotes differentiation of preosteoblast cells into osteoblasts to induce production of mineralized nodules, but also, at the same time, inhibits differentiation of bone marrow cells into osteoclasts and the function of osteoclasts so that bone homeostasis is effectively regulated.

In addition, the present invention relates to a pharmaceutical composition for preventing or treating a menopausal disease, in particular, a menopausal bone disease; and the pharmaceutical composition is very effective in preventing or treating a menopausal bone-related disease in that it not only increases the volume of trabecular bone and promotes differentiation of preosteoblast cells into osteoblasts to induce production of mineralized nodules, but also, at the same time, inhibits differentiation of bone marrow cells into osteoclasts and the function of osteoclasts so that bone homeostasis is effectively regulated.

The invention claimed is:

1. A method for ameliorating or treating a menopausal bone disease, the method comprising administering to a subject as an active ingredient a steroid sulfatase inhibitor represented by Formula 2:

[Formula 2]

2. The method according to claim 1, wherein the menopausal bone disease is at least one selected from the group consisting of type I osteoporosis due to menopause, type I osteoporosis due to ovarian extraction, spinal stenosis, spinal compression fracture, and osteoarthritis.

3. The method according to claim 1, wherein the method increases the volume of trabecular bone.

4. The method according to claim 1, wherein the method promotes differentiation of preosteoblast cells into osteoblasts.

5. The method according to claim 1, wherein the method inhibits differentiation of bone marrow cells into osteoclasts.

* * * * *